US009644176B2

(12) United States Patent
Henderson

(10) Patent No.: US 9,644,176 B2
(45) Date of Patent: May 9, 2017

(54) PHOTOBIOREACTOR

(71) Applicant: KELLOGG BROWN & ROOT LLC, Houston, TX (US)

(72) Inventor: Garry Henderson, Indooroopilly (AU)

(73) Assignee: KELLOGG BROWN & ROOT LLC, Houston, TX (US)

( * ) Notice: Subject to any disclaimer, the term of this patent is extended or adjusted under 35 U.S.C. 154(b) by 0 days.

(21) Appl. No.: 14/352,732

(22) PCT Filed: Oct. 19, 2012

(86) PCT No.: PCT/AU2012/001280
§ 371 (c)(1),
(2) Date: Apr. 18, 2014

(87) PCT Pub. No.: WO2013/056317
PCT Pub. Date: Apr. 25, 2013

(65) Prior Publication Data
US 2014/0256022 A1   Sep. 11, 2014

(30) Foreign Application Priority Data

Oct. 19, 2011   (AU) .............................. 2011904323

(51) Int. Cl.
*C12M 1/00* (2006.01)
*C12M 1/04* (2006.01)
*B01D 53/84* (2006.01)
*C12N 1/12* (2006.01)

(52) U.S. Cl.
CPC ............. *C12M 21/02* (2013.01); *B01D 53/84* (2013.01); *C12M 23/24* (2013.01); *C12M 31/02* (2013.01); *C12M 31/10* (2013.01); *C12M 43/04* (2013.01); *C12N 1/12* (2013.01)

(58) Field of Classification Search
CPC ...... C12M 21/02; C12M 23/24; C12M 31/02; C12M 31/10; C12M 43/04; B01D 53/84; C12N 1/12
See application file for complete search history.

(56) References Cited

U.S. PATENT DOCUMENTS

2005/0064577 A1*  3/2005  Berzin ................... B01D 53/85
                                                          435/266
2009/0148931 A1*  6/2009  Wilkerson et al. .... C12M 21/02
                                                          435/286.1

* cited by examiner

*Primary Examiner* — Gautam Prakash
(74) *Attorney, Agent, or Firm* — Gary Machetta

(57) ABSTRACT

A photobioreactor has an optical waveguide formed at least in part from a highly scattering optically transmitting polymer. The optical waveguide has a light distributing part immersed in a container holding photoactive biological material and a light collecting part outside the container.

13 Claims, 4 Drawing Sheets

PHOTOBIOREACTOR

FIELD OF THE INVENTION

The present invention relates to the field of photobioreactors More particularly, the invention relates to a photobioreactor that utilizes highly scattering optically transmitting (HSOT) polymers for light diffusion.

BACKGROUND TO THE INVENTION

A bioreactor is a device or system that supports a biologically active environment. For example, a bioreactor may be a vessel in which a chemical process is carried out which involves organisms or biochemically active substances derived from such organisms. The chemical process may be aerobic or anaerobic and the system may be closed or open. Bioreactors may range in size from liters to cubic meters.

A photobioreactor (PBR) is a bioreactor which incorporates some type of light source. Photobioreactors are used to grow small phototrophic organisms such as cyanobacteria, algae, or moss plants. These organisms use light through photosynthesis as their main energy source and do not require sugars or lipids as energy source. The term PBR is commonly used to define a closed system in which the walls of the container are translucent. This configuration is selected so that sunlight can penetrate the walls of the container. A PBR may also be an open system such as an open tank or pond but this presents a greater challenge for delivery of appropriate levels of light to sustain the photo-reactions.

In both cases, open systems and closed systems, the level of light delivered is critical to the efficiency of the bioreactor. It is desirable to use sunlight as the primary source of photo energy as it is free and abundant. However, if too little light is delivered the organisms die or too little photosynthesis occurs to be useful. On the other hand, if too much sunlight is delivered it is detrimental to the organisms. It has been reported that sunlight is 4 to 5 times too intense for most species of micro-algae.

It is expected that for enhanced efficiency sunlight needs to be diluted and evenly distributed throughout the photobioreactor. Known photobioreactors, such as that described in International Patent Publication WO 2010/132955, describe systems for collecting and intensifying sunlight but do not adequately address distributing the sunlight in the photobioreactor. Other known arrangements, such as described in International Patent Publication WO 2010/077638, merely use a cylindrical waveguide to transport the collected sunlight to a greater depth in a photobioreactor container or open pond, they do not address even distribution of the sunlight.

Carbon emissions have become an issue in many countries. In recent years a number of countries have introduced carbon trading schemes in an effort to encourage emmitters to reduce carbon emissions. These schemes have the potential to improve the economic viability of the commercial scale use of photobioreactors.

OBJECTS OF THE INVENTION

It is an object of the present invention to overcome or at least alleviate one or more of the above limitations.

It is a further object of the invention to provide an efficient and/or economic photobioreactor.

SUMMARY OF THE INVENTION

In one form, although it need not be the only or indeed the broadest form, the invention resides in a photobioreactor comprising:
a container holding a photoactive biological material; and
an optical waveguide at least partially located within the container;
wherein the optical waveguide is formed at least in part from highly scattering optically transmitting polymer.

Suitably the waveguide is formed with a light collecting part and a light distributing part. The light distributing part suitably is formed entirely from the highly scattering optically transmitting polymer and is located wholly within the container. The light collecting part is suitably outside the container and is formed from a low diffusion optical material, such as polymer or glass.

Suitably the light distributing part provides a light dilution factor of about 2 to 6 times.

The container may be an open system, such as a pond, or a closed system, such as a cell. In one particular form, at least one wall of the container is gas permeable and liquid impermeable.

In a further form the invention resides in a method of operating a photobioreactor including the steps of:
forming a waveguide having a light collecting part and a light distributing part, the light collecting part being formed from a low diffusion optical material and the light distributing part being formed from highly scattering optically transmitting polymer;
locating at least a portion of the light distributing part in a container;
filling the container with photoactive biological material;
collecting sunlight through the light collecting part; and
transmitting the collected sunlight to the light distributing part.

The light distributing part preferably provides a light diffusion of between 2 and 6 times.

Further features and advantages of the present invention will become apparent from the following detailed description.

BRIEF DESCRIPTION OF THE DRAWINGS

To assist in understanding the invention and to enable a person skilled in the art to put the invention into practical effect, preferred embodiments of the invention will be described by way of example only with reference to the accompanying drawings, in which.

DETAILED DESCRIPTION OF THE INVENTION

Figure 1:
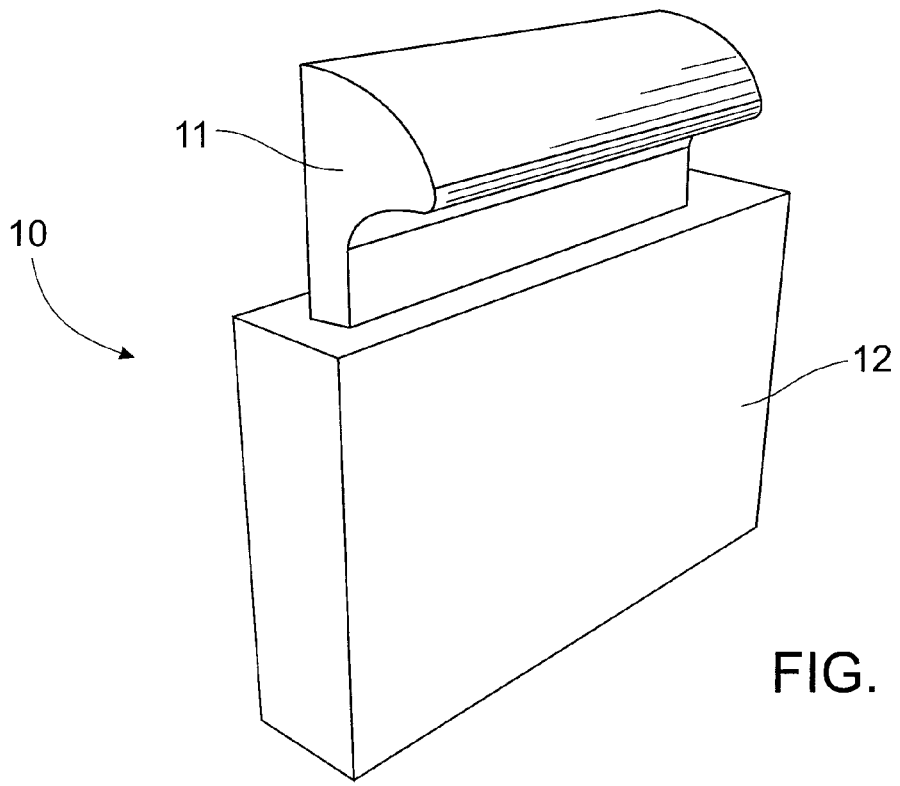
FIG. 1 is a schematic of one embodiment of a photobioreactor.

Embodiments of the present invention reside primarily in a photobioreactor. Accordingly, the elements have been illustrated in concise schematic form in the drawings, showing only those specific details that are necessary for understanding the embodiments of the present invention, but so as not to obscure the disclosure with excessive detail that will be readily apparent to those of ordinary skill in the art having the benefit of the present description.

In this specification, adjectives such as first and second, left and right, and the like may be used solely to distinguish one element or action from another element or action without necessarily requiring or implying any actual such relationship or order. Words such as "comprises" or "includes" are intended to define a non-exclusive inclusion, such that a process, method, article, or apparatus that comprises a list of elements does not include only those elements but may include other elements not expressly listed, including elements that are inherent to such a process, method, article, or apparatus.

Figure 2:
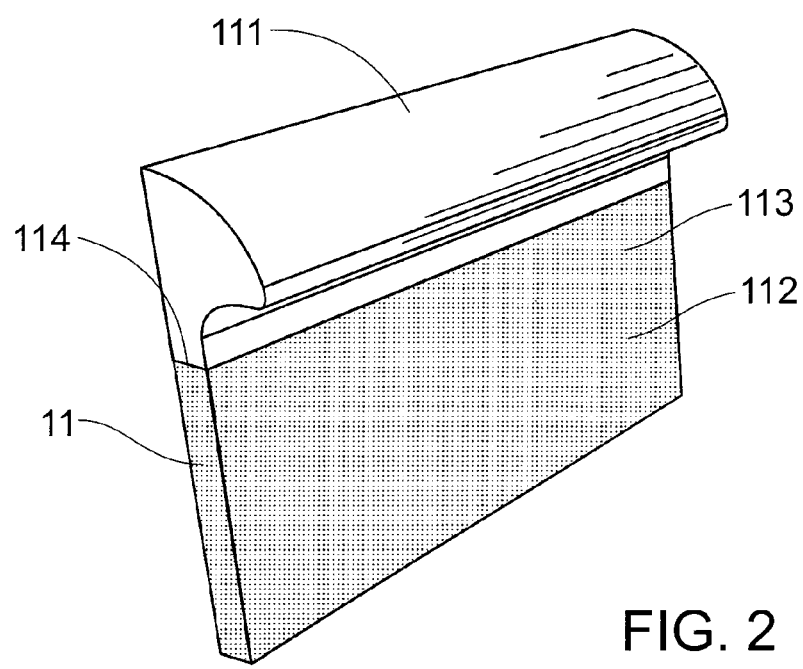
FIG. 2 shows one embodiment of the waveguide of the photobioreactor of FIG. 1.

Referring to FIG. 1 there is shown a schematic of a photobioreactor 10 consisting of a waveguide 11 suspended in a container 12. The waveguide 11, in the embodiment shown, is made of a light transmitting plastics material such as polymethylmethacrylate although glass and other materials may be suitable. A light collecting part of the waveguide 111 (as seen most clearly in FIG. 2) is shaped for maximum sunlight collection and a light distributing part 112 is shaped for maximum distribution of sunlight into the container. The inventor has found that the light distributing part 112 is suitably a sheet and the light collecting part 111 should be enlarged to enhance collection efficiency.

Sunlight collected by the light collecting part 111 is guided to the light distributing part 112. The light distributing part 112 is formed from highly scattering optical transmission (HSOT) polymer. HSOT polymers are formed by introducing heterogeneous structures on the order of microns into photonics polymers. These micro-structures are too small to be discernible but for the purpose of exemplification are shown as dots 113 in FIG. 2. Light injected into the HSOT polymers is multiply scattered maintaining its directivity due to the heterogeneous structures and then homogeneously emitted as a directed scattered light. HSOT polymers have been successfully used in backlights of liquid crystal displays (LCDs).

The light collecting part 111 of the waveguide is shaped to maximize light capture for a given location. The inventor envisages the light collecting part 111 being specifically designed for a particular location such that each location will have a different shaped light collecting part 111. The captured sunlight is directed into the light distributing part 112. It is anticipated that in most situations the intensity of light directed to the light distributing part 112 would be 4 to 5 times too intense for most species of micro-algae. However, the size ratio of the light collecting part 111 to the light distributing part 112 means that the collected sunlight is distributed over an area 4 to 5 times greater than the collection area, thus diluting the light to a level that is not detrimental to the micro-algae while at the same time distributing the light to a greater depth. The HSOT polymer achieves homogeneous distribution of light into the container 12.

Depending on the specific design of the light collecting part 111 and the size of the light distributing part 112, the light dilution factor may be about 2 times, or 3 times, or 4 times, or 5 times, or 6 times. The invention is not limited to these specific values but the inventor envisages that in many applications these values will be typical.

The light collecting part 111 may be produced from a flexible polymer so that it can be flexed to track the sun. Alternatively only a portion, such as the portion indicated as 114 in FIG. 2, may be flexible so that the light collecting part 111 can be flexed to track the sun. Suitable flexible polymeric materials include, for example, polyethylene, polypropylene, polyurethane, polycarbonate, polyvinylpyrrolidone, polyvinylchloride, polystyrene, poly(ethylene terephthalate), poly(ethylene naphthalate), poly(1,4-cyclohexane dimethylene terephthalate), polyolefin, polybutylene, polyacrylate, and polyvinlyidene chloride. The flexible polymeric material or film may be in the form of a single layer (comprising a single polymer or several polymers), or may comprise several polymer layers (of the same or different composition), such as a composite polymeric film.

Alternatively the light collecting part 111 may be formed from a rigid light transmitting material such as glass or a rigid polymer. Rigid polymeric materials that may be used include, for example, thermoplastic polymers such as polycarbonates, poly(meth)acrylates such as polymethyl methacrylate, polyolefins such as polyethylene and polypropylene, polyesters such as polyethyleneterephthalates and polyethylenenaphthalates, celluloseacetate, polyvinyl chloride, and copolymers of acrylonitrile, styrene and butadiene.

Whether the light collecting part 111 is rigid or flexible it may be useful to allow it to move relative to the light distributing part 112 in a manner which tracks the sun to optimise the amount of incident sunlight throughout the day. Whatever the actual connection between the light collecting 111 and light distributing 112 parts, it should not significantly diminish the transmittal of received light between these parts while allowing for the necessary sun tracking movement.

Figure 3:
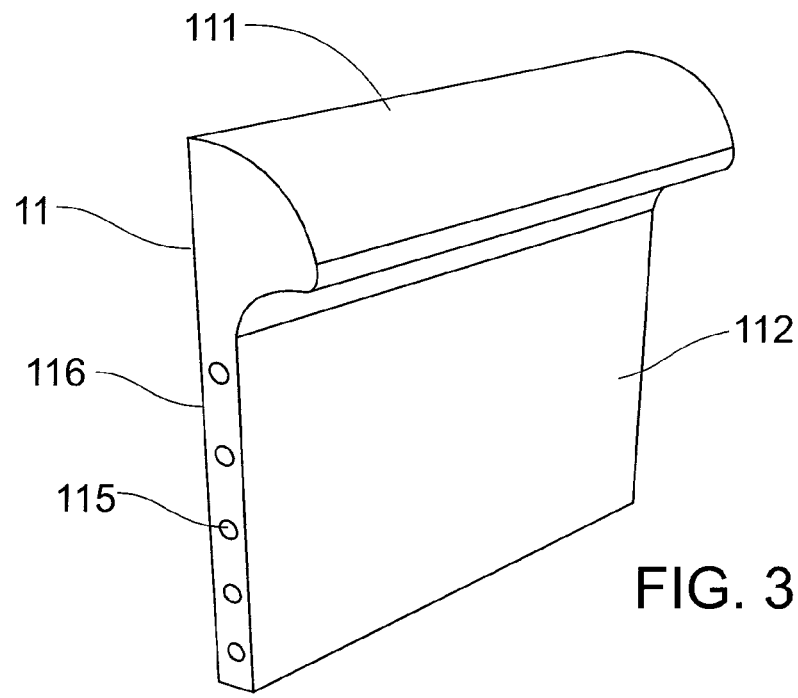
FIG. 3 shows another embodiment of the waveguide of the photobioreactor of FIG. 1 incorporating a supplemental light source.

Even with the use of solar tracking technology to maximise sunlight collection it may be the case that prolonged overcast periods or other low light conditions means that the photobioreactor 10 does not operate efficiently. In such circumstances it may be advantageous to supplement sunlight by using supplemental light sources. One suitable supplemental light source is shown in FIG. 3. In FIG. 3 a number of light emitting diodes (LED) 115 typically operating in the visible region from about 400 nm to about 700 nm, although not limited thereto, are arranged to direct light into a side 116 of the light distributing part 112. The LED could also be used to compensate for seasonal variation thus maintaining a constant production efficiency of the photobioreactor 10 throughout the year.

A wide range of micro-algae are suitable for use in the photobioreactor. For example, lipid or oil-producing algae include a wide variety of algae, such as the diatoms (bacillariophytes), green algae (chlorophytes), blue-green algae (cyanophytes), and golden-brown algae (chrysophytes). Exemplary bacillariophytes capable of oil production include the genera *Amphipleura, Amphora, Chaetoceros, Cyclotella, Cymbella, Fragilaria, Hantzschia, Navicula, Nitzschia, Phaeodactylum*, and *Thalassiosira*. Exemplary chlorophytes capable of oil production include the genera *Ankistrodesmus, Botryococcus, Chlorella, Chlorococcum, Dunaliella, Monoraphidium, Oocystis, Scenedesmus*, and *Tetraselmis*. Exemplary cyanophytes capable of oil production include the genera *Oscillatoria* and *Synechococcus*. An example of a chrysophyte capable of oil production is the genera *Boekelovia*. A combination of two or more strains of algae can be used in the photobioreactor embodiments described herein.

Many micro-algae have peak production efficiency in a narrow wavelength range. To maximise efficiency of the photobioreactor a wavelength shifting dopant may be incorporated into the light collecting part 111 of the waveguide 11. The dopant is chosen for the wavelength shift required for a given organism. Generally this will require a shift from the blue end of the spectrum (short wavelengths) to the red end of the spectrum (long wavelengths).

The container 12 may contain water having simple organic carbon compounds that the given species of micro-algae are able to utilize. This may include acetic acid or simple sugars. This allows the bioreactor to be operated in a mixotrophic mode. That is, part of the bioreactor operates in autotrophic (photosynthetic) mode and part in heterotrophic (respirating) mode. It has been reported that mixotrophic mode can produce 3 to 4 times the biomass of autotrophic mode alone.

The photobioreactor 10 may form part of a closed system with the fluid medium supporting micro-photosynthetic organisms on each side of the light distributing part 112 constrained by gas permeable membranes. The membranes define a photobioreactor container that contains the growth media. The photobioreactor 10 is then placed within a gas carrying duct. The carbon dioxide rich flue gas is directed over the gas permeable membranes of the photobioreactor 40. Gas exchange with the media within the membrane occurs based on concentration gradients. The media acts as a sink of carbon dioxide, some oxides of nitrogen, and oxides of sulphur. The appropriate photosynthetic organism is selected for the particular gas mix being treated.

Figure 4:
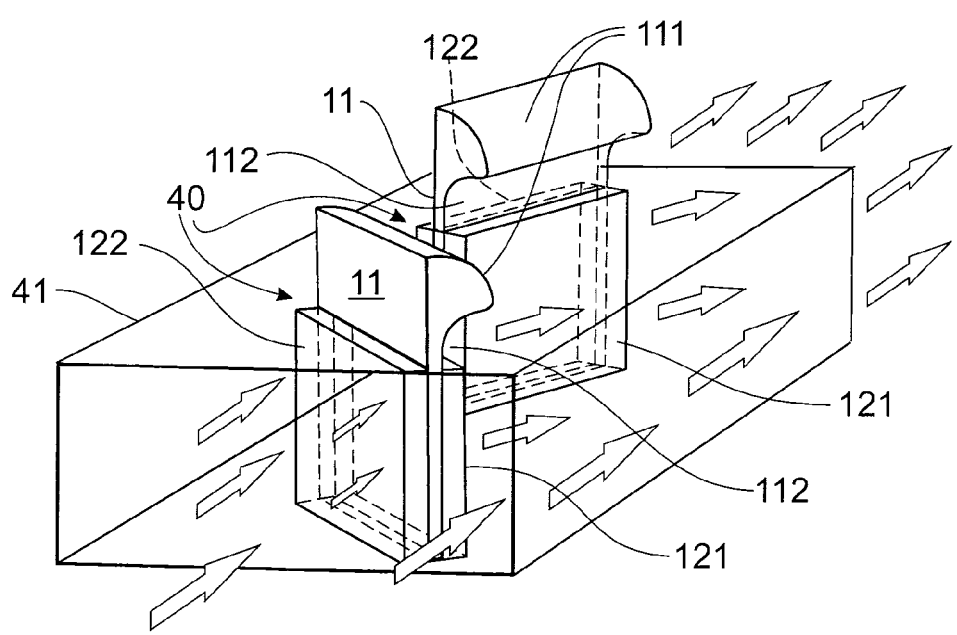
FIG. 4 is a schematic of another embodiment of a photobioreactor in a flue duct.

As mentioned above, the photobioreactor 10 may be an open system or a closed system, such as a number of photobioreactors 40 as shown in FIG. 4. In FIG. 4, each photobioreactor is formed by a waveguide 11 having the same structure as described earlier. That is, the waveguide 11 has a light collection part 111 formed from a low diffusion optical material and a light distributing part 112 formed from highly scattering optically transmitting polymer. The waveguide 11 is suspended in a container 12 having two opposed walls 121, 122 formed from a gas permeable but liquid impermeable material. The walls 121, 122 permit gas to pass through but contain the photoactive growth media within the container 12. Each of the photobioreactors 40 is located in a duct 41 that contains flue gases, non-limiting examples of which may include carbon monoxide, carbon dioxide, oxides of nitrogen and oxides of sulphur. The upper and lower walls of the container 12 are in contact with the floor and ceiling of the duct 41. It will be appreciated that there may be any suitable number of photobioreactors 40 located within the duct 41.

In FIG. 4 the two photobioreactors 40 shown are placed in relation to the walls of the duct 41 and to each other to maximise the exposure of gas permeable faces 121, 122 to the flue gas. The open V-shape created by the relationship of the photobioreactors 40, one to the other, is designed to generate something of a serpentine flow of the flue gas to improve exposure time although it will be appreciated that other designs would be acceptable. There may be rows of individual photobioreactors with each row placed at an angle to the next row in a manner which optimises the flue gas transfer for an individual circumstance.

Figure 5:
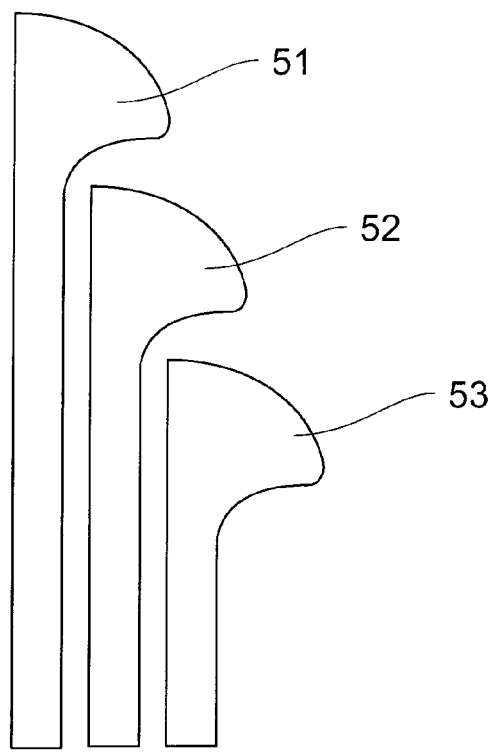
FIG. 5 is a schematic of stacked waveguides.

In an open system the container 12 will generally be larger, such as a pond. To maximise production a larger surface area of waveguide 11 is required. The waveguides may be stacked such as shown in FIG. 5. Each waveguide 51, 52, 53 will have a light collecting part 111 having different lengths to transmit the light to essentially equal sized light distributing part 112, as shown. The uppermost waveguide 51 is seen to have the largest light transmitting section to an equal sized part 112 and so efficiency losses would be expected to be higher than for waveguides 52 and 53. This is compensated for by waveguide 51 presenting the largest exposed light collecting part 111 to incident light. In many instances, the multiple waveguide arrangement shown in FIG. 5 may be repeated in a linear fashion to produce repeating units in a manner similar to the layout of single light guides which is shown repeated linearly in FIG. 6.

Figure 6:
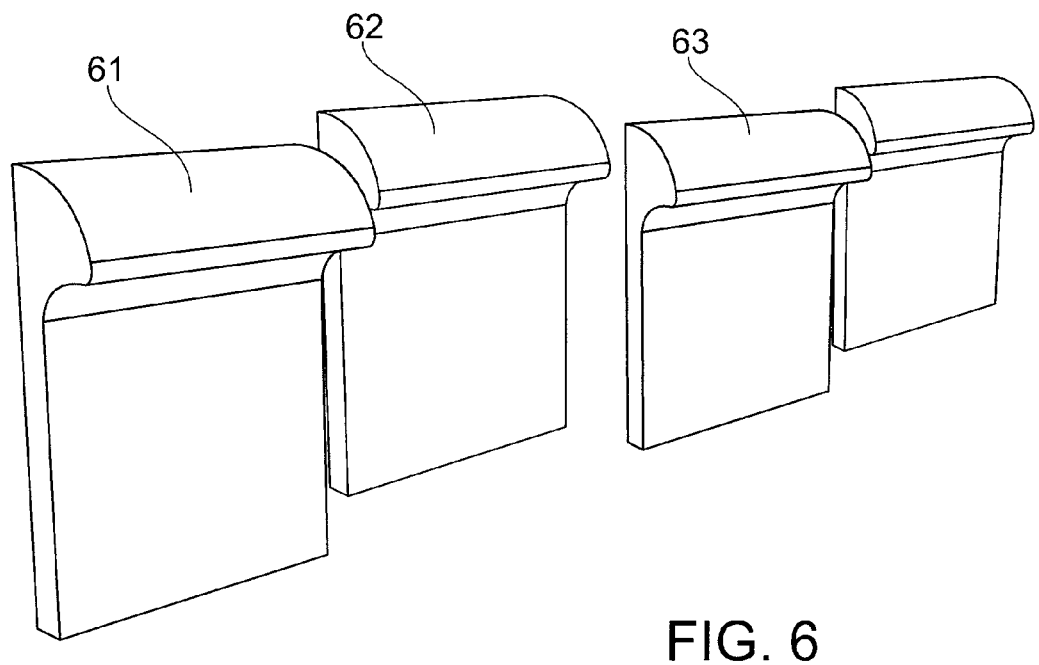
FIG. 6 is a schematic of aligned waveguides.

In the embodiment shown in FIG. 6 the waveguides 61, 62, 63 are the same size and are arranged side by side. The waveguides 61, 62, 63 are suitably aligned parallel with the direction of flow of media so that hydraulic losses are minimised.

Figure 7:
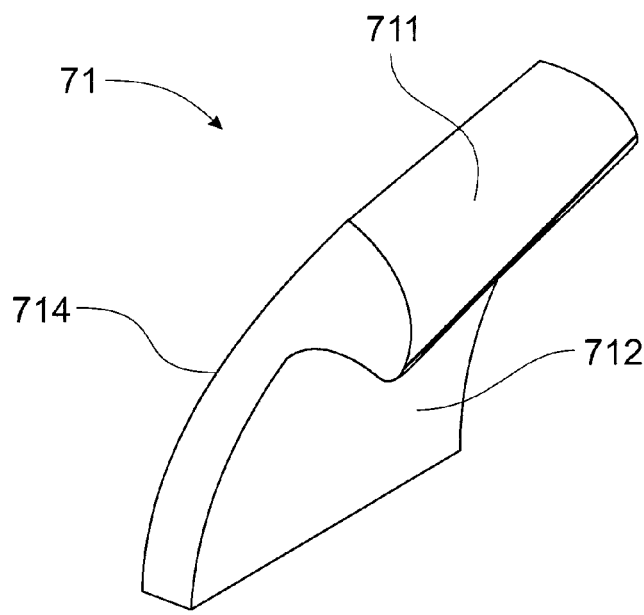
FIG. 7 shows a further embodiment of the waveguide.

A further embodiment of the waveguide is shown in FIG. 7. The waveguide 71 comprises a light collecting part 711 and a light distributing part 712. The light collecting part 711 and the light distributing part 712 are connected by a transition part 714. The transition part 714 may be flexible in the manner mentioned above with respect to FIG. 2. The transmission part 714 is twisted so that light collecting part 711 and the light distributing part 712 are angled with respect to each other. The waveguide of FIG. 7 may be useful in application where the container must take a particular orientation (such as fitting to an existing flue) but the light collecting part 711 must point in a different direction to collect sunlight. The embodiment will also be useful to track the sun throughout the year. The angle difference between the solstices can be 45 degrees. Because the light collecting part 711, transition part 714 and light distributing part 712 form a waveguide there is no requirement for alignment of the light collecting part 711 and light distributing part 712. The transition part 714 may be a semi-flexible polymer material that can be set to a position during installation.

Figure 8:
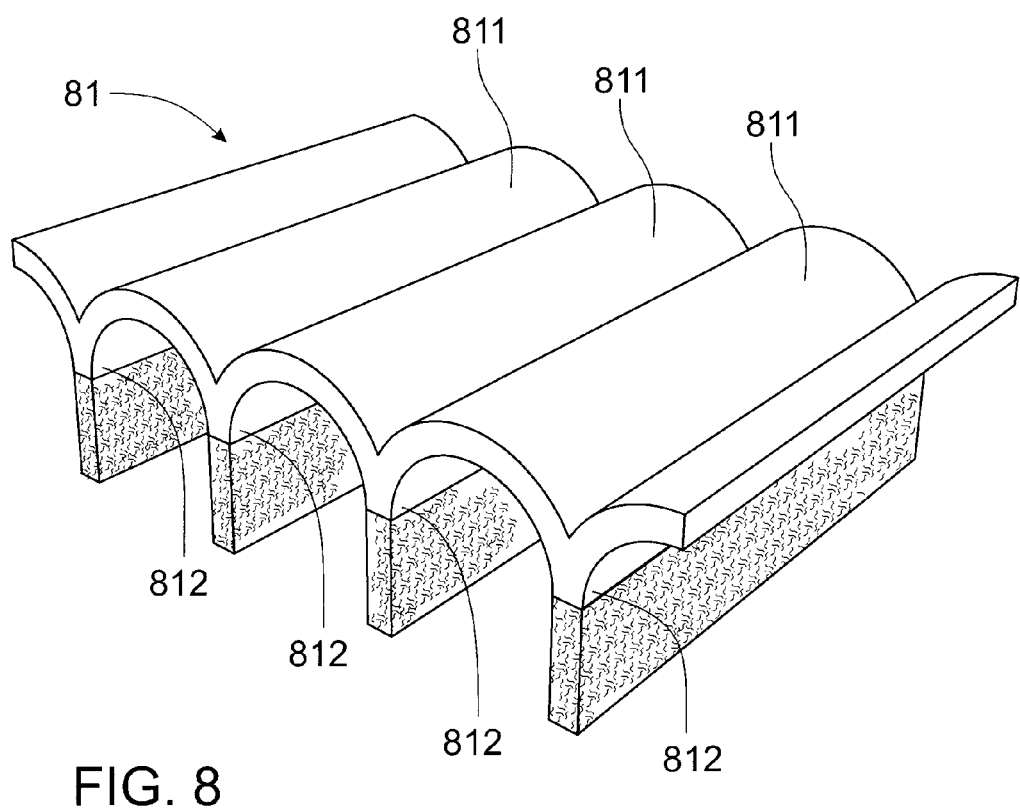
FIG. 8 shows a still further embodiment of a waveguide well suited to a photobioreactor installation.

A yet further embodiment of a waveguide is shown in FIG. 8. The waveguide 81 comprises three waveguides combined into a single structure. Thus there are three light distributing parts 812 joined by two light collecting parts 811. The light distributing parts 812 are each formed from highly scattering optical transmission polymer, as described earlier. The light distributing parts 812 may be immersed in individual containers (not shown) or in a single larger container. The shape of the light collecting parts 811 will be optimised for a location to provide efficient collection of sunlight. The light collecting part 811 may be formed from any suitable low diffusion optical material as described earlier. It will be appreciated that this embodiment is not limited to three light distributing parts 812 linked by two light capturing parts 811, but can be scaled to any number of light distributing and light capturing parts. The light collecting part at each end of the waveguide may take a different shape from that shown or may be omitted so the light collecting parts terminate at a light distributing part at each end.

FIG. 8 shows the shape of the surfaces of the light collecting parts being the same above and below, but the light collecting part may have different shaped surfaces on the upper surface and the lower surface, depending upon the optical properties of the material used and the latitude of where the unit is to be sited. Indeed, the specific shape of the light collecting part will be chosen to suit the particular site.

Certain embodiments may also use optical coatings on the waveguide to reduce or increase reflection as required. For instance, in the embodiment of FIG. 8, the underside of the curved light collecting part may be HR (high reflection) coated and the upper side may be AR (anti-reflection) coated. The high reflection coating may be a mirror. In some embodiments it will also be appropriate to provide a mirror coating on the waveguide around the transition from the light collecting part to the light distributing part to minimize losses. Arrangements to enhance light collection, such as reflectors and lenses may also be provided to increase the flux of sunlight collected by the light collection part. Other arrangements will be readily apparent to persons skilled in the art.

A technical advantage of the invention described here is that it allows the dilution of sunlight in a manner that prevents the waste of available light. Dilution of the light also eliminates the need to provide energy intensive mixing to prevent light fatigue of the photo-organisms. Distribution of sunlight deeper into a photobioreactor allows algal growth at greater depth than hitherto achievable.

The invention will find many applications. One example is to economically treat municipal and industrial wastewaters using mixotrophic micro-algae to produce renewable fuel feedstock. Such an application can be incorporated in new designs for wastewater treatment facilities or retrofitted to existing facilities. This approach provides water utilities with a method of reducing their greenhouse gas footprint and to recover dilute resources from wastewaters.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this invention is intended to embrace all alternatives, modifications and variations of the present invention that have been discussed herein, and other embodiments that fall within the spirit and scope of the above described invention.

The invention claimed is:

1. A photobioreactor that uses sunlight as a light source, comprising:
   a container holding a photoactive biological material; and
   an optical waveguide at least partially located within the container;
   wherein the optical waveguide is formed at least in part from highly scattering optically transmitting polymer, and
   wherein the optical waveguide is formed with a light collecting part contacting a light distributing part, the light collecting part having a surface configured to collect the sunlight, wherein the light distributing part is formed as a sheet, wherein the light collecting part and the light distributing part have a fixed size ratio, and wherein the light collection part has a first surface configured to collect sunlight and second surface directly directing the collected sunlight into a side of the sheet that the light collection part contact.

2. The photobioreactor of claim 1 wherein the light distributing part is formed entirely from the highly scattering optically transmitting particles.

3. The photobioreactor of claim 1 wherein the light distributing part is located wholly within the container.

4. The photobioreactor of claim 1 wherein the light collecting part is located wholly outside the container.

5. The photobioreactor of claim 1 wherein the light collecting part and the light distributing part have a size ratio selected to provide a light dilution factor of about 2 to 10 times.

6. The photobioreactor of claim 1 wherein the waveguide includes at least a portion that is a flexible part.

7. The photobioreactor of claim 1 wherein the waveguide is doped with wavelength shifting dopant.

8. The photobioreactor of claim 1 wherein the container is a cell having at least one wall that is gas permeable and liquid impermeable.

9. The photobioreactor of claim 1, wherein the light distributing part is a sheet and the light collection part injects the collected sunlight along a side of the sheet.

10. The photobioreactor of claim 1 further comprising supplemental light sources that direct light into the waveguide.

11. The photobioreactor of claim 10 wherein the supplemental light sources are light emitting diodes positioned to inject light into the light distributing part along a side that is different from a side along which the light collecting part contacts the light distributing part.

12. A photobioreactor that uses sunlight, comprising:
   a container holding a photoactive biological material, and
   an optical waveguide at least partially located within the container, wherein the optical waveguide is formed as a sheet that has a light collecting part and a light distributing part,
   wherein the light distributing part is formed in part of a highly scattering optically transmitting polymer,
   wherein the light collection part has a surface configured to collect sunlight and to direct the collected sunlight into a side of the sheet that the light collection part contacts, and
   wherein the optical wave guide has only one light collecting part and one light distributing part, wherein the light collecting part and the light distributing part have a size ratio selected to provide a light dilution factor of about 2 to 6 times.

13. The photobioreactor of claim 12, wherein all of the light collected by the light collecting part is directed into the one light distributing part.

* * * * *